US009999442B2

(12) United States Patent
Lattouf

(10) Patent No.: US 9,999,442 B2
(45) Date of Patent: Jun. 19, 2018

(54) METHODS FOR ACCESSING A LEFT VENTRICLE

(71) Applicant: Omar M. Lattouf, Atlanta, GA (US)

(72) Inventor: Omar M. Lattouf, Atlanta, GA (US)

(73) Assignee: Trans Cardiac Therapeutics, Inc., Duluth, GA (US)

( * ) Notice: Subject to any disclaimer, the term of this patent is extended or adjusted under 35 U.S.C. 154(b) by 709 days.

(21) Appl. No.: 13/871,505

(22) Filed: Apr. 26, 2013

(65) Prior Publication Data
US 2013/0253641 A1 Sep. 26, 2013

Related U.S. Application Data

(63) Continuation of application No. 13/247,304, filed on Sep. 28, 2011, which is a continuation of application
(Continued)

(51) Int. Cl.
*A61B 17/34* (2006.01)
*A61F 2/24* (2006.01)
(Continued)

(52) U.S. Cl.
CPC ...... *A61B 17/3423* (2013.01); *A61B 17/3421* (2013.01); *A61B 17/3462* (2013.01);
(Continued)

(58) Field of Classification Search
CPC .... A61B 2017/00243; A61B 17/00234; A61B 2017/00247; A61B 2018/00392;
(Continued)

(56) References Cited

U.S. PATENT DOCUMENTS 3,844,292 A 10/1974 Bolduc
3,952,742 A 4/1976 Taylor
(Continued)

FOREIGN PATENT DOCUMENTS

WO WO 98/07375 A1 2/1998
WO WO 99/00059 A1 1/1999
(Continued)

OTHER PUBLICATIONS

International search report dated Jul. 3, 2003 for PCT/US2002/039087.
(Continued)

*Primary Examiner* — Christopher L Templeton
(74) *Attorney, Agent, or Firm* — Wilson Sonsini Goodrich & Rosati

(57) ABSTRACT

Two minimally invasive therapeutic procedures, particularly for patients with congestive heart failure, may be performed separately or together. One procedure involves providing a valved passageway through the patient's left ventricular wall at the apex of the patient's heart and advancing instruments through the valved passageway to connect the valve leaflets of the patient's heart valve, e.g. the mitral valve. The second procedure involves advancing a pacing lead and a pacing lead implanting device through a trocar in the patient's chest and implanting the pacing lead on an exposed epicardial region of the patient's heart wall. The pacing lead has a penetrating electrode which is secured within the heart wall. Improved devices for these procedures include a minimally invasive grasping device for heart leaflets, a leaflet connector with artificial cordae tendenae and a pacing lead implant instrument.

10 Claims, 17 Drawing Sheets

Related U.S. Application Data

No. 12/006,967, filed on Jan. 8, 2008, which is a continuation-in-part of application No. 11/784,385, filed on Apr. 6, 2007, which is a continuation-in-part of application No. 10/313,198, filed on Dec. 6, 2002, now Pat. No. 7,373,207, which is a continuation-in-part of application No. 10/295,390, filed on Nov. 15, 2002, now Pat. No. 6,978,176.

(60) Provisional application No. 60/369,988, filed on Apr. 4, 2002, provisional application No. 60/365,918, filed on Mar. 20, 2002, provisional application No. 60/340,062, filed on Dec. 8, 2001.

(51) Int. Cl.
| | |
|---|---|
| *A61B 18/14* | (2006.01) |
| *A61M 39/06* | (2006.01) |
| *A61B 18/02* | (2006.01) |
| *A61B 18/18* | (2006.01) |
| *A61B 18/24* | (2006.01) |
| *A61B 17/00* | (2006.01) |
| *A61B 18/00* | (2006.01) |

(52) U.S. Cl.
CPC ........ *A61B 18/1492* (2013.01); *A61F 2/2427* (2013.01); *A61B 17/3498* (2013.01); *A61B 18/02* (2013.01); *A61B 18/18* (2013.01); *A61B 18/24* (2013.01); *A61B 2017/00278* (2013.01); *A61B 2017/3425* (2013.01); *A61B 2017/3486* (2013.01); *A61B 2017/3492* (2013.01); *A61B 2018/00351* (2013.01); *A61B 2018/00357* (2013.01); *A61F 2/2442* (2013.01); *A61F 2/2454* (2013.01); *A61F 2/2457* (2013.01); *A61F 2250/0097* (2013.01); *A61M 39/06* (2013.01); *A61M 2039/0646* (2013.01)

(58) Field of Classification Search
CPC .. A61B 2017/00278; A61B 2017/3427; A61B 17/34; A61B 17/3421; A61B 17/3423; A61B 17/3492; A61B 17/3488; A61B 17/3482; A61B 17/348; A61B 17/3425; A61B 17/3498; A61M 39/06; A61M 2039/0626; A61M 2039/0646
USPC .................. 604/506, 509, 101.05; 600/184; 606/119, 172, 194; 607/130; 623/1.14, 623/1.24, 1.26, 2.1, 2.11, 2.38
See application file for complete search history.

(56) References Cited

U.S. PATENT DOCUMENTS

| | | | |
|---|---|---|---|
| 4,207,903 A | 6/1980 | O'Neill | |
| 4,280,510 A | 7/1981 | O'Neill et al. | |
| 4,357,946 A | 11/1982 | Dutcher et al. | |
| 4,424,818 A | 1/1984 | Doring et al. | |
| 4,475,560 A | 10/1984 | Tarjan et al. | |
| 4,936,304 A | 6/1990 | Kresh et al. | |
| 5,336,252 A | 8/1994 | Cohen | |
| 5,536,252 A | 7/1996 | Imran et al. | |
| 5,571,215 A | 11/1996 | Sterman et al. | |
| 5,618,287 A | 4/1997 | Fogarty et al. | |
| 5,665,109 A | 9/1997 | Yoon | |
| 5,716,392 A | 2/1998 | Bourgeois et al. | |
| 5,758,664 A | 6/1998 | Campbell et al. | |
| 5,766,163 A | 6/1998 | Mueller et al. | |
| 5,797,933 A * | 8/1998 | Snow et al. | 606/151 |
| 5,799,661 A * | 9/1998 | Boyd | A61B 17/00234 |
| | | | 128/898 |
| 5,824,071 A * | 10/1998 | Nelson et al. | 606/194 |
| 5,855,592 A | 1/1999 | McGee et al. | |
| 5,860,951 A | 1/1999 | Eggers et al. | |
| 5,904,711 A | 5/1999 | Flom et al. | |
| 5,924,424 A | 7/1999 | Stevens et al. | |
| 5,964,793 A | 10/1999 | Rutten et al. | |
| 5,978,714 A | 11/1999 | Zadini et al. | |
| 5,980,455 A * | 11/1999 | Daniel | A61B 17/00234 |
| | | | 600/201 |
| 5,990,382 A * | 11/1999 | Fox | A61B 10/00 |
| | | | 623/16.11 |
| 6,010,526 A | 1/2000 | Sandstrom et al. | |
| 6,079,414 A * | 6/2000 | Roth | 128/898 |
| 6,087,394 A | 7/2000 | Duhaylongsod | |
| 6,120,520 A | 9/2000 | Saadat et al. | |
| 6,139,555 A | 10/2000 | Hart et al. | |
| 6,162,195 A | 12/2000 | Igo et al. | |
| 6,224,617 B1 | 5/2001 | Saadat et al. | |
| 6,231,518 B1 | 5/2001 | Grabek et al. | |
| 6,258,069 B1 | 7/2001 | Carpentier et al. | |
| 6,258,083 B1 | 7/2001 | Daniel et al. | |
| 6,258,105 B1 | 7/2001 | Hart et al. | |
| 6,269,819 B1 | 8/2001 | Oz et al. | |
| 6,345,198 B1 | 2/2002 | Mouchawar et al. | |
| 6,401,720 B1 | 6/2002 | Stevens et al. | |
| 6,409,759 B1 | 6/2002 | Peredo | |
| 6,620,181 B1 | 9/2003 | Bonutti | |
| 6,629,534 B1 | 10/2003 | Goar St. | |
| 6,682,499 B2 | 1/2004 | Lenker | |
| 6,978,176 B2 | 12/2005 | Lattouf | |
| 6,997,950 B2 | 2/2006 | Chawla | |
| 7,146,225 B2 | 12/2006 | Guenst et al. | |
| 7,270,669 B1 | 9/2007 | Sra | |
| 7,373,207 B2 | 5/2008 | Lattouf | |
| 7,513,908 B2 | 4/2009 | Lattouf | |
| 7,534,260 B2 | 5/2009 | Lattouf | |
| 7,721,742 B2 | 5/2010 | Kalloo et al. | |
| 7,871,433 B2 | 1/2011 | Lattouf | |
| 8,029,565 B2 | 10/2011 | Lattouf | |
| 2001/0049497 A1 | 12/2001 | Kalloo et al. | |
| 2002/0042564 A1* | 4/2002 | Cooper | A61B 8/12 |
| | | | 600/407 |
| 2002/0161378 A1 | 10/2002 | Downing | |
| 2002/0165606 A1* | 11/2002 | Wolf et al. | 623/1.24 |
| 2003/0032979 A1* | 2/2003 | Mortier et al. | 606/213 |
| 2003/0105519 A1 | 6/2003 | Fasol et al. | |
| 2004/0092984 A1* | 5/2004 | Parihar | A61B 17/3421 |
| | | | 606/167 |
| 2006/0004323 A1 | 1/2006 | Chang et al. | |
| 2006/0074484 A1 | 4/2006 | Huber | |
| 2006/0095025 A1 | 5/2006 | Levine et al. | |
| 2006/0287716 A1 | 12/2006 | Banbury et al. | |
| 2007/0027534 A1 | 2/2007 | Bergheim et al. | |
| 2007/0118151 A1 | 5/2007 | Davidson | |
| 2007/0270793 A1 | 11/2007 | Lattouf | |
| 2008/0004597 A1 | 1/2008 | Lattouf et al. | |
| 2008/0147184 A1 | 6/2008 | Lattouf | |
| 2008/0249504 A1 | 10/2008 | Lattouf et al. | |
| 2011/0144743 A1 | 6/2011 | Lattouf | |
| 2012/0203072 A1 | 8/2012 | Lattouf et al. | |

FOREIGN PATENT DOCUMENTS

| | | |
|---|---|---|
| WO | WO 99/11201 A2 | 3/1999 |
| WO | WO 00/60995 A2 | 10/2000 |
| WO | WO 01/28432 A1 | 4/2001 |

OTHER PUBLICATIONS

International search report dated Nov. 11, 2002 for PCT/US2002/028101.
Office action dated Jan. 4, 2005 for U.S. Appl. No. 10/295,390.
Office action dated Jan. 26, 2010 for U.S. Appl. No. 12/384,260.
Office action dated Feb. 16, 2012 for U.S. Appl. No. 12/006,967.
Office action dated Feb. 28, 2013 for U.S. Appl. No. 13/247,304.
Office action dated Mar. 6, 2007 for U.S. Appl. No. 10/313,198.
Office action dated Mar. 6, 2013 for U.S. Appl. No. 12/006,967.
Office action dated Mar. 22, 2010 for U.S. Appl. No. 12/070,680.
Office action dated Apr. 29, 2010 for U.S. Appl. No. 12/384,260.

(56) References Cited

OTHER PUBLICATIONS

Office action dated May 25, 2011 for U.S. Appl. No. 11/784,385.
Office action dated Jun. 9, 2006 for U.S. Appl. No. 10/313,198.
Office action dated Jun. 23, 2011 for U.S. Appl. No. 12/006,967.
Office action dated Aug. 8, 2008 for U.S. Appl. No. 11/285,469.
Office action dated Aug. 13, 2008 for U.S. Appl. No. 11/285,438.
Office action dated Aug. 16, 2010 for U.S. Appl. No. 11/784,681.
Office action dated Sep. 28, 2006 for U.S. Appl. No. 10/313,198.
Office action dated Nov. 4, 2005 for U.S. Appl. No. 10/313,198.
Office action dated Nov. 15, 2010 for U.S. Appl. No. 11/784,385.

* cited by examiner

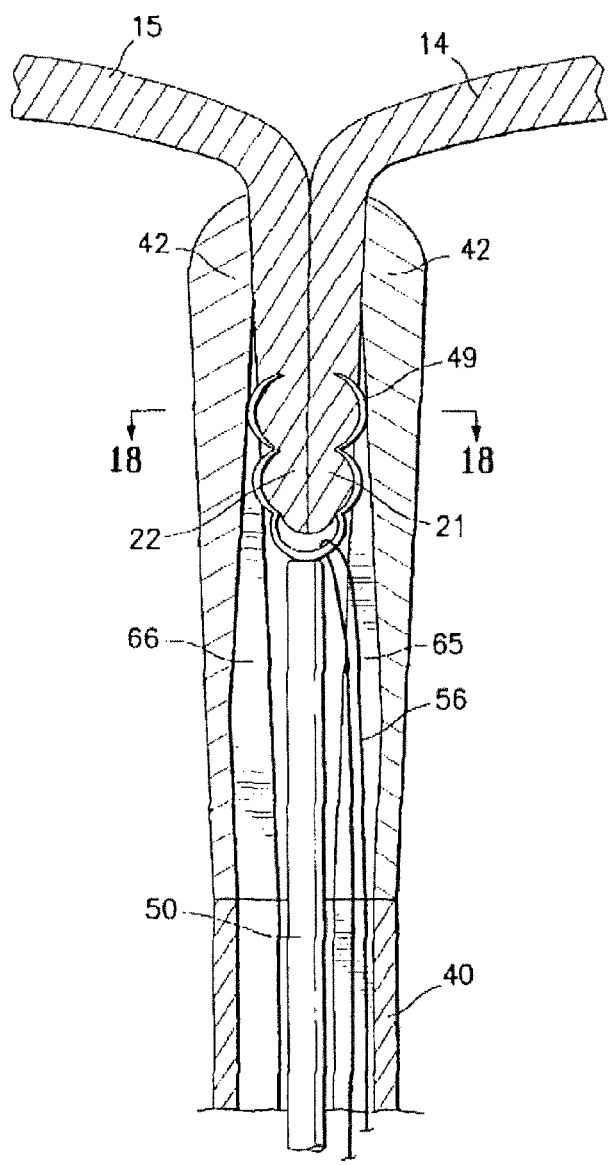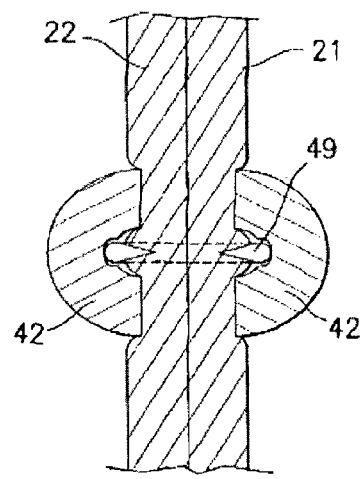
FIG. 17
FIG. 18

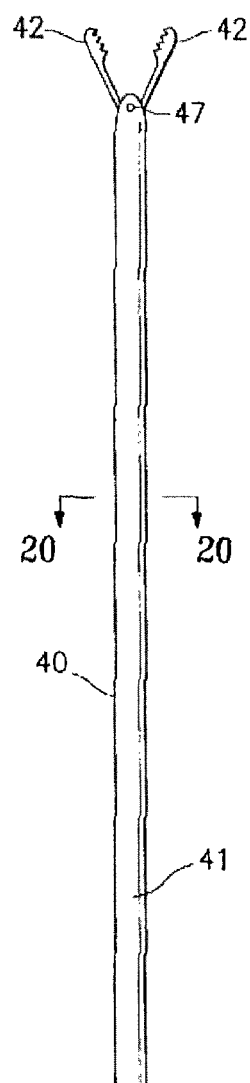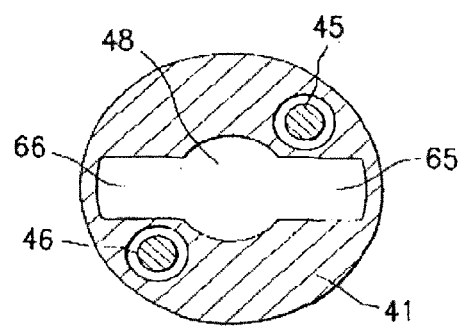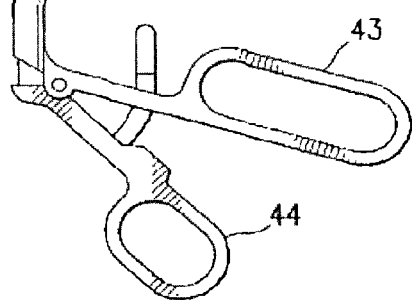
FIG. 19
FIG. 20

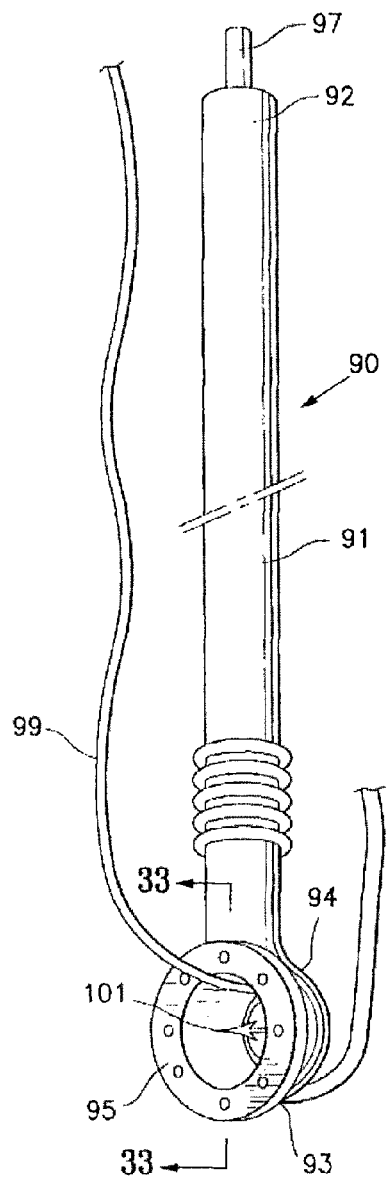
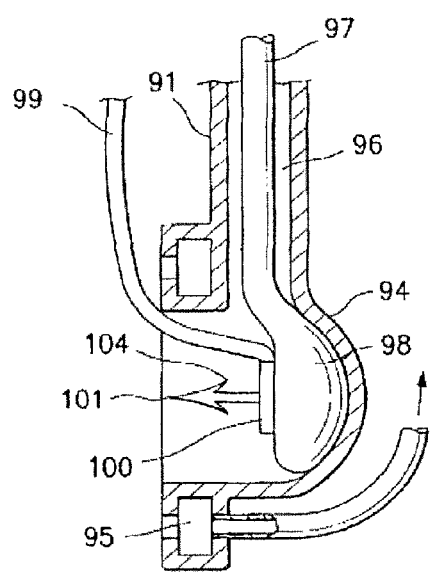
FIG. 32
FIG. 33

METHODS FOR ACCESSING A LEFT VENTRICLE

CROSS-REFERENCE TO RELATED APPLICATION

This application is a continuation of application Ser. No. 13/247,304, filed on Sep. 28, 2011, which was a continuation of application Ser. No. 12/006,967, filed Jan. 8, 2008, which was a continuation in part of application Ser. No. 11/784,385, filed on Apr. 6, 2007, which was a continuation in part of application Ser. No. 10/313,198, filed on Dec. 6, 2002 (now U.S. Pat. No. 7,373,207), which was a continuation in part of application Ser. No. 10/295,390, filed on Nov. 15, 2002 (now U.S. Pat. No. 6,978,176) which claimed priority from provisional application Ser. No. 60/340,062, filed Dec. 8, 2001; provisional application Ser. No. 60/365,918, filed Mar. 20, 2002; and provisional application Ser. No. 60/369,988, filed Apr. 4, 2002. All of these applications are incorporated herein by reference in their entirety. The specification of the present application is identical to that of application Ser. No. 10/295,390, filed on Nov. 15, 2002 (now U.S. Pat. No. 6,978,176).

BACKGROUND OF THE INVENTION

This invention is directed to therapeutic procedures for a patient's heart and to instruments and systems for such procedures. The procedures and the instruments and systems for such procedures are particularly suitable for treating that patient suffering from the symptoms of congestive heart failure (CHF), and particularly to those CHF patients exhibiting mitral valve regurgitation (MVR) and/or those exhibiting intraventricular conduction delay with resulting disturbance of the synchronous right and/or left ventricular contractility.

There are over five million patients in the United States suffering from congestive heart failure and there are more than seven hundred thousand new cases each year. For many of these patients medical therapy is not very successful. Recent trials have shown that a significant number of CHF patient's benefit from percutaneous ventricular pacing where pacing leads are introduced percutaneously and advanced within the patient's vasculature until the leads are disposed within the patient's coronary sinus. However, ventricular pacing has not been found successful for a significant number of CHF patients for a variety of reasons. For example, in a number of procedures the coronary sinus cannot be cannulate and even if cannulated, the leads can become displaced.

With many CHF patients, their ventricular ejection fraction is reduced due to mitral valve regurgitation (MR) resulting from dilated cardiomyopathy, which is the deformity of the heart which accompanies CHF. The MR in turn can exacerbate the cardiomyopathy leading to a worsening of the MR. The MR can also be the result of torn cordae tendenae which can also prevent complete closure of the valve.

Surgical procedures for mitral valve repair for MR typically involves valve support ring at the base of valve. Recent advances in valve repair include securing together the free edges of the mitral valve leaflets by sutures staples and the like, commonly called "Bow-Tie" or "edge to edge" techniques. These procedures usually involve open heart surgery including cardiopulmonary bypass and a sternotomy, although more recently some of these procedures have been performed by minimally invasive and percutaneous techniques which can reduce the morbidity of such procedures. Percutaneous procedures impose difficulties in instrument design because the instruments for such procedures must be long enough, have small enough profile and have sufficient flexibility for advancement through the patient's vasculature into the patient's heart chamber. However, they must also be able to accurately locate the operative ends of such instruments at a desired location within the chambers of the patient's beating heart and be strong enough to perform the required functions.

Techniques for Bow-Tie repair of mitral valves have been mentioned in the patent literature, but specific instruments for such techniques are not yet commercially available.

BRIEF SUMMARY OF THE INVENTION

This invention generally relates to minimally invasive therapeutic procedures, including valve repair and ventricular pacing, for patients with CHF and to the devices and systems suitable for use in such procedures. Specifically, one aspect of the invention is directed to gaining access to a patient's heart chamber through the wall of the patient's heart, such as at the apex thereof, for repairing damaged or otherwise incompetent heart valves. The invention is also directed to the attachment of a pacing lead to an exterior region of the patient's heart wall for ventricular pacing. These procedures provided alone and particularly when performed together provide significant relief and longer life to symptomatic CHF patients. Moreover, due to the minimally invasive nature of these procedures, many of the CHF patient population, who are otherwise unsuitable for conventional treatments, may be treated with the present procedures.

While the procedure is primarily described herein for repairing damaged or otherwise incompetent valves between chambers of the patient's heart, the procedure can be employed in a variety of treatments or diagnoses within the patient's heart chambers. Other procedures which may be performed include transmyocardial revascularization, aortic stenting for aortic dissections and aneurysm therapy, removal or clots and vegetations of prosthetic valves, excision of heart tumors, stem cell and vascular growth factor implantation, ventricular septal defect closure and the like.

The procedure related to valve repair generally includes first gaining access to the patient's chest cavity through a small opening made in the patient's chest to gain access the chest cavity, preferably though an intercostal space between two of the patient's ribs. Such accessing can be effected thoroscopically through an intercostal space between the patient's ribs by minimally invasive procedures wherein a trocar or other suitable device is placed within the passageway in the patient's chest to the patient's chest cavity.

The patient's heart wall is pierced to provide a passageway through the heart wall to a heart cavity such as the left ventricle, defined in part by the pierced heart wall. Preferably, the passageway is formed through a region of the heart wall at or near the apex of the patient's heart. Suitable piercing elements include a 14 gauge needle. A guide wire is advanced through the inner lumen of the needle into the heart chamber and further advanced through the valve to be treated into an adjacent heart chamber. The needle may then be removed leaving the guide wire in place. A valve is advanced over the guide wire and installed in the ventricular wall passageway which is configured to enable passage of instruments for the procedure through the heart wall into the heart chamber while preventing loss of blood through the passageway. The valve may be permanently or temporarily within the heart wall passageway. A dog-boned shape balloon can be utilized to seat the securing elements of the valve within the passageway.

The instruments for performing the procedure may then be passed through the valve seated in the passageway. The proximal ends of these instruments extend out of the patient to allow the instruments to be manipulated to more accurately position the operative ends of the instruments at the desired location within the heart chamber to perform the procedure and to operate the operative member which may be provided on the distal ends of these instruments.

An expandable stabilizing instrument is provided to stabilize the tissue structure within the heart chamber at a grasping location, such as the mitral valve leaflets upon which the procedure is to be performed. In the case of mitral or atrioventrical valve repair, the stabilizing instrument is a catheter having one or more expandable members on a distal location thereof, such as an inflatable balloon or expandable arms, which can engage the atrial surface of the valve leaflets to stabilize and urge the valve leaflets toward a grasping location in the left ventricle to allow the grasping member to engage and hold the valve leaflets together so that the free ends of the leaflets can be secured together by suitable leaflet connecting elements. Suitable leaflet connecting elements include clips, staples, and the like. The distal extremity of the catheter having the expandable member is advanced into the atrial chamber. The expandable member(s) e.g. an inflatable balloon or one or more arms or struts are expanded and then the catheter is pulled proximally to engage the expandable member(s) against the atrial side of the valve leaflets and push the leaflets into the grasping location within the ventricular chamber.

An elongated grasping device with at least a pair of grasping members such as jaws on the distal end thereof for grasping tissue structure is advanced through the valve until the distal end extends out of the distal end of the guiding catheter. The grasping members or jaws of the grasping device are operated from the proximal end of the grasping device which extends out the proximal end of the guiding catheter extending out of the patient. The jaws of the grasping device are opened to engage the stabilized valve leaflets in the grasping location and then closed to grip the leaflets so that the free edges of the valve leaflets are placed into an operative position for the Bow-Tie repair. The free ends of the grasped valve leaflets may be joined or otherwise secured together by suitable connecting elements such as clips, staples and the like. Once the free edges of the valve leaflets are secured together, the instruments for the procedure may be withdrawn through the valve in the heart wall and then the opening in the patient's chest. The valve will close upon instrument removal to eliminate or at least minimize blood leakage through the valve. The valve may be left in place or removed and the passageway sutured closed.

When there is cordae tendenae damage with the heart valve, particularly when there is severance of the cordae tendenae from the valve leaflet or the papillary muscle, repair of the valve leaflet, even by means of the Bow-Tie technique, may not prevent reshaping of the ventricular architecture which can reduce ventricular output. In that instance, it has been found that providing an artificial cordae tendenae such as a strand extending between the valve leaflets and the heart wall in generally the same orientation as the cordae tendenae will support the connected valve leaflets in more or less a normal manner to minimize ventricular deformation (e.g. dilation) which leads to decreased output. One end of the strand is secured to the connecting element securing the free edges of the valve leaflets or to the free edges themselves and the other end of the strand is secured to a location on the heart wall, preferably on the exterior of the heart wall. The strand should be relatively inelastic or non-compliant to ensure an effective closed position of the leaflets. In this case it is preferred that the passageway through the ventricular wall pass through the apex region of the heart between the two papillary muscles in the left ventricle, so that the pull on the valve leaflets by the strand secured to the leaflets is in approximately the same angle or orientation as the natural pull by the competent cordae tendenae. This provides for a better seal of the leaflets and thereby minimizes leakage through the valve.

Other procedures which may also be performed through the seated valve in the heart wall passageway in addition to valve repair include transmyocardial revascularization where a tissue ablation instrument is advanced into the heart chamber for ablating tissue in an ischemic region of the ventricular wall. It is generally thought that the tissue ablation in the ischemic region causes angiogenesis and thus revascularization which returns blood flow to the region. For TMR procedures in some regions of the heart chamber, a secondary or subselective guiding catheter having a pre-shaped distal tip may be needed to orient the ablating tip to the desired ischemic region of the patient's heart wall. A similar procedure may be utilized to ablate regions of the intraventricular wall to terminate or curtail arrhythmia. Other procedures are contemplated.

The minimally invasive placement of a pacing lead having a penetrating electrode is performed through a small opening in the patient's chest in the intercostal space between ribs. The small opening is preferably provided with a suitable trocar such as those available commercially. The distal end of the pacing lead is introduced into the patient's chest cavity through the trocar and the penetrating electrode on the distal end of the pacing lead is inserted into an exposed epicardial surface on the patient' ventricular wall which defines the heart chamber such as the left ventricle. The pericardium is removed from the region to expose the epicardium. The proximal end of the pacing lead is configured to be connected to an electrical power source such as those used for pacing purposes which produce a pulsed electrical output of suitable frequency, current and voltage levels to control the contraction of the ventricular wall to which the pacing lead is attached. The pacing lead may be tunneled subcutaneously to the power source. The penetrating electrode preferably has hooks or other suitable structures for preventing removal of the electrode from the heart wall. The penetrating electrode may take the form of an arrow, fish-hook or helical coil. Other shapes are suitable.

The devices suitable for installing the pacing lead in the exterior of the heart wall are configured to be advanced through the trocar or small opening in the patient's chest and press or otherwise put the penetrating electrode of the pacing lead within the ventricular wall.

The output from the paced heart chamber is greatly increased and in conjunction with a repaired valve preventing or minimizing regurgitation, the CHF patient has a significant improvement in physical well being, life extension and quality of life.

These and other advantages of the invention will become more apparent from the following detailed description and accompanying exemplary drawings.

BRIEF DESCRIPTION OF THE DRAWINGS

The invention has other advantages and features which will be more readily apparent from the following detailed description of the invention and the appended claims, when taken in conjunction with the accompanying drawings, in which:

FIG. 17 is an enlarged view of the distal end of the grasping device as shown in FIG. 16 with a clip is position partially pressed into a connecting relationship with the free edges of the valve leaflets.

FIG. 18 is a transverse cross-sectional view taken along the lines 18-18 shown in FIG. 17 illustrating the clip partially connected to the valve leaflets.

FIG. 19 is an elevational view of a grasping device embodying features of the invention.

FIG. 20 is a transverse cross-sectional view of the grasping device shown in FIG. 19 taken along the lines 20-20.

FIGS. 32 and 33 illustrate an alternative embodiment of a minimally invasive device for implating a pacing lead in a patient's heart wall.

The drawings are for the most part schematic presentations and not to scale.

DETAILED DESCRIPTION OF THE INVENTION

Figure 1:
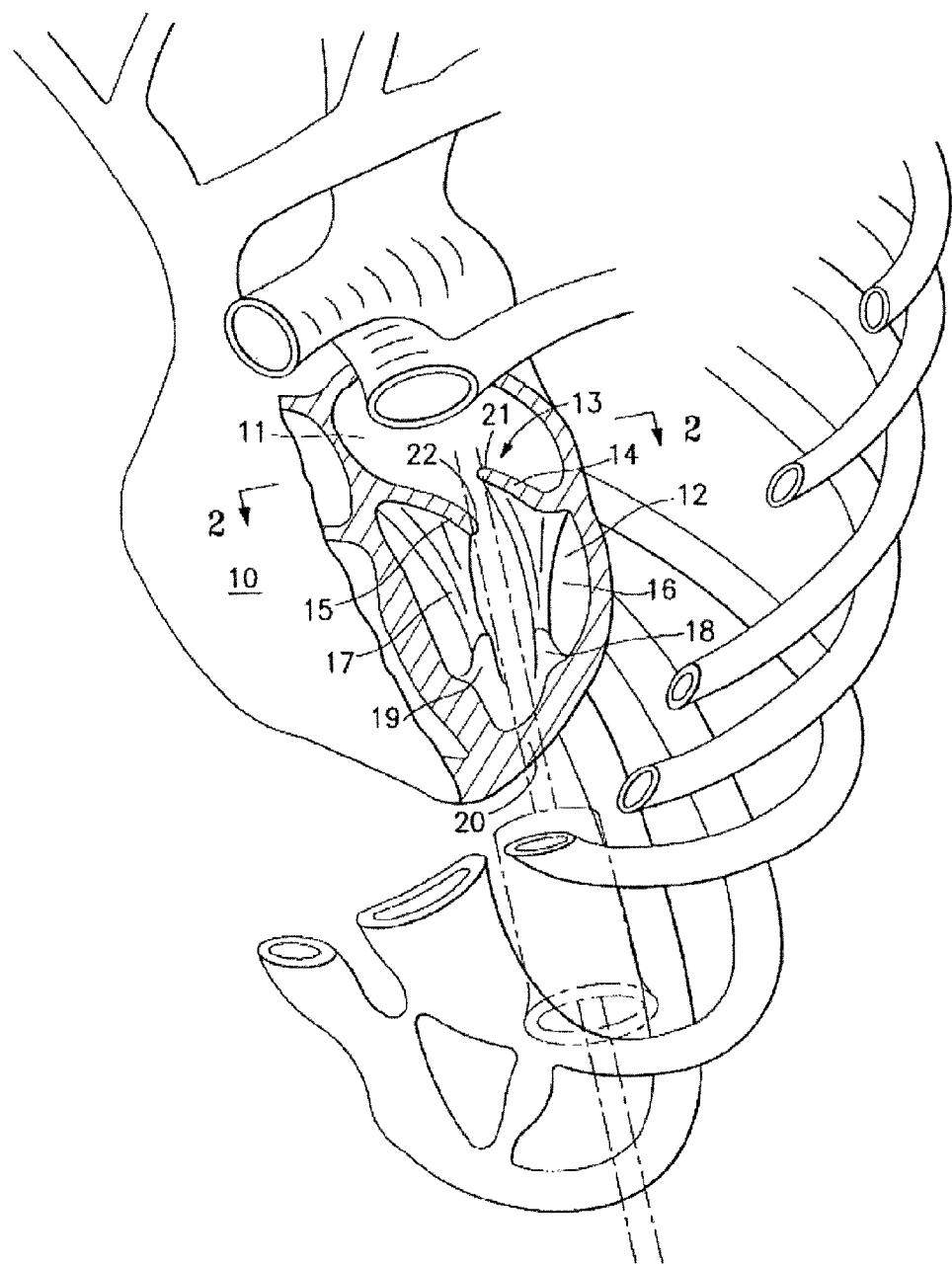
FIG. 1 is a perspective view of a patient's chest, partially illustrating the location of the patient's heart within the chest cavity, with part of the heart wall removed to expose the left ventricular chamber and illustrate torn cordae tendenae connected to one of the valve leaflets.

FIG. 1 illustrates a patient's heart 10 with the left side of the heart in partial cross-section schematically showing the patient's left atrium 11 and left ventricle 12 with a mitral valve 13 disposed between the left atrium and the left ventricle having a posterior valve leaflet 14 and an anterior leaflet 15. Each of the valve leaflets 14 and 15 have cordae tendenae 16 and 17 respectively which are connected to the leaflets and to papillary muscles 18 and 19 respectively within the left ventricle at the apex 20 of the heart. The posterior leaflet 14 of the mitral valve 13 is shown with its cordae tendenae 16 partially torn. The free edge 21 of the posterior leaflet is uncontrolled due to the torn cordae tendenae which makes the valve incompetent to close completely when the heart contracts during systole. This result in regurgitation of blood back through the valve which in turn results in lowered blood output for the left ventricle. The anterior valve leaflet 16 is shown with its cordae tendenae 17 completely attached.

Figure 2A:
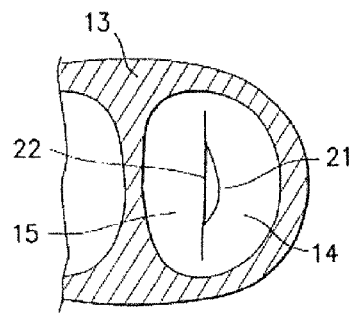
FIG. 2A is a transverse cross-sectional view taken along the lines 2-2 shown in FIG. 1 illustrating the incompetent mitral valve in a closed condition during systole.
Figure 2B:
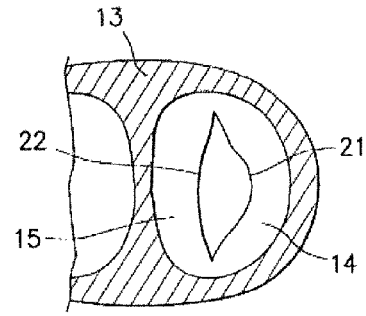
FIG. 2B is a transverse cross-sectional view taken along the lines 3-3 shown in FIG. 2 illustrating the incompetent valve in an open condition during diastole.

FIGS. 2A and 2B illustrate the closed and open condition respectively of an incompetent mitral valve 13 such as that shown in FIG. 1. The free edge 21 of posterior valve leaflet 14 is unable to close completely against the free edge 22 of anterior leaflet 15 due to the torn cordae tendenae as depicted in FIG. 1. A similar leaflet condition may occur due to dilated ventricular architecture, i.e. dilated cardiomyopathy, characteristic of congestive heart failure.

Figure 3A:
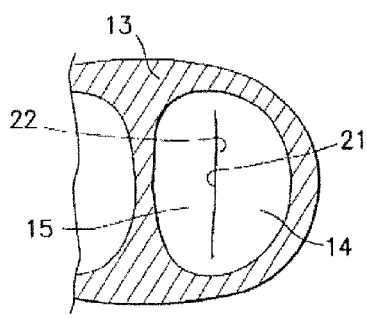
FIGS. 3A and 3B are transverse cross-sectional views similar to those shown in FIGS. 2A and 2B but of a competent mitral valve.
Figure 3B:
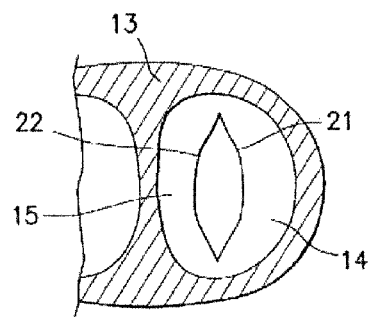

FIG. 3A illustrates a healthy competent mitral valve 13 with valve leaflets 14 and 15 which is closed completely during systole to prevent regurgitation of blood through the valve. FIG. 3B illustrates the competent mitral valve shown in FIG. 2A in an opened condition during diastole to allow blood to flow from the left atrium to the left ventricle.

Figure 4A:
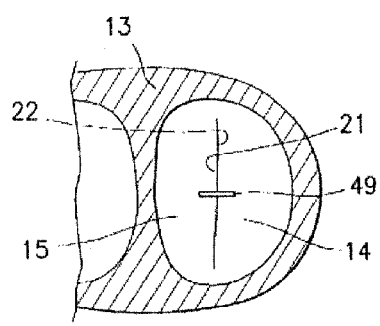
FIGS. 4A and 4B are transverse cross-sectional views similar to those shown in FIGS. 2A and 2B wherein the valve leaflets are secured together in a "Bow-Tie" configuration.
Figure 4B:
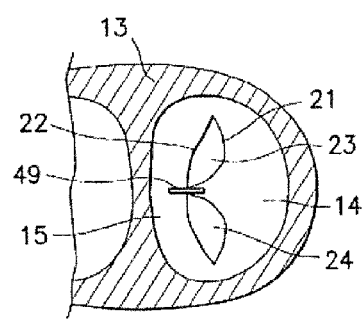
Figure 26:
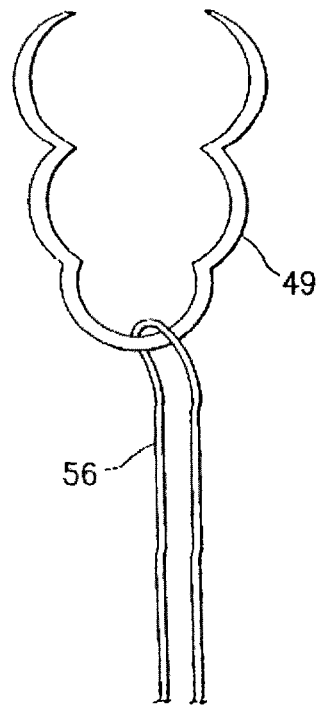
FIG. 26 is an enlarged elevational view of the clip with a artificial cordae tendenae strand secured to the closed end of the clip.

FIGS. 4A and 4B illustrate the closed and opened conditions of a mitral valve 13 in which the free edge 21 of posterior valve leaflet 14 and the free edge 22 of the anterior leaflet valve 15 are secured together in a Bow-Tie connection by a suitable clip 49, such as is shown in FIG. 26. During systole when the heart contracts, the clip holds the free edges 21 and 22 of the valve leaflets together to minimize blood regurgitation through the valve. However, during diastole, when the heart muscle relaxes and the blood pressure within the left ventricle is reduced, the mitral valve 13 opens up much like a competent valve but with two openings 23 and 24 between the valve leaflets 14 and 15. The interference with blood flow through the two openings 23 and 24 of a repaired mitral valve with a Bow-Tie connection between the leaflets is minimal compared to the flow with a single opening for a competent mitral valve.

Figure 5:
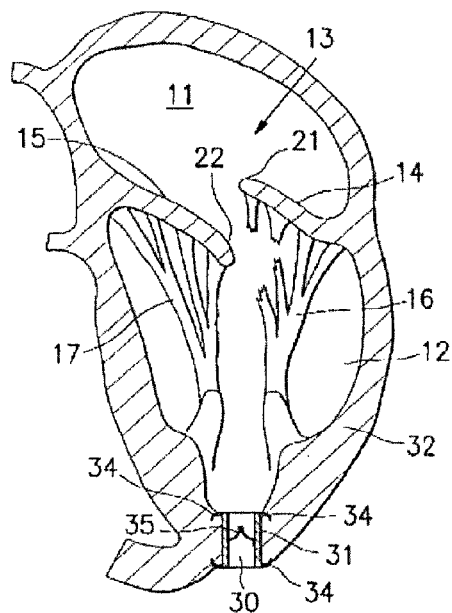
FIG. 5 is a partial elevational view in section of a patient's left ventricle illustrating a valve seated in the apical ventricular wall.
Figure 7:
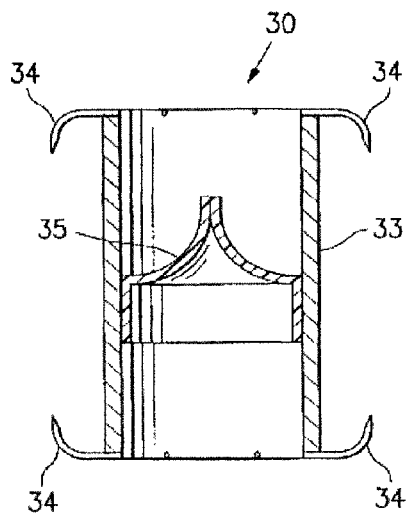
FIG. 7 is a longitudinal cross-sectional view taken along the lines 7-7 shown in FIG. 6.
Figure 6:
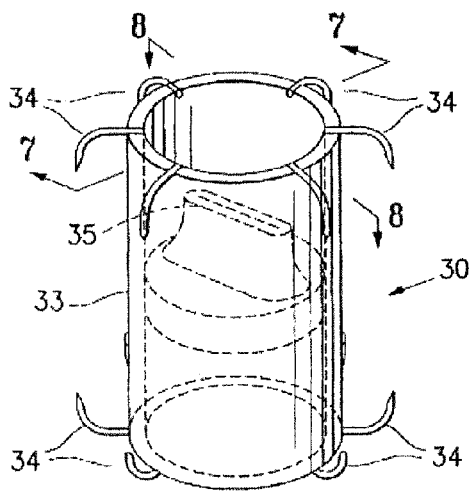
FIG. 6 is an enlarged perspective view of the valve shown in FIG. 5.
Figure 8:
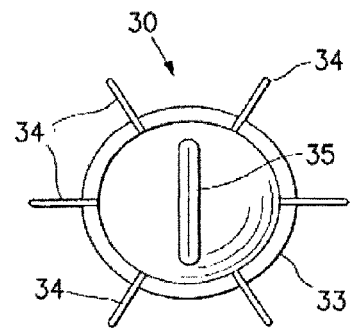
FIG. 8 is a top view of the valve taken along the lines 8-8 shown in FIG. 6.
Figure 9:
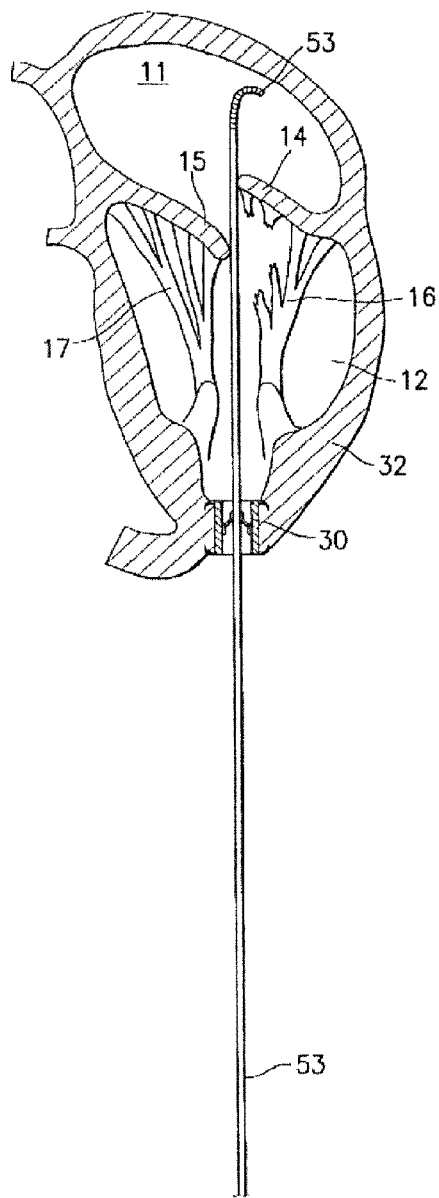
FIG. 9 is a partial elevational view, in section of the left side of the patient's heart illustrating the positioning of a guide wire in the patient's heart interior with the shaped distal tip of a guide wire in the patient's left atrium.

FIG. 5 illustrates a left side of a patient's heart such as is shown in FIG. 1 with an incompetent mitral valve 13 due to torn cordae tendenae 14. A valve 30 embodying features of the invention is deployed within a passageway 31 through the free ventricular heart wall 32. An entrance to the valve 13 is flush with an outer surface of the heart and an exit from the valve is flush with an inner surface of the left ventricle of the heart. As is shown in more detail in FIGS. 6-8, the valve 30 has a cylindrical structure 33 which is secured within the passageway 31 by elements 34 which may be barbs or hooks. The valve component 35 of valve 30 is a duck billed valve component formed of polymeric material which allow the passage of instruments for deployment or treatment but prevent or at least minimize loss of blood through the heart wall. The cylindrical structure 33 may be in a form similar to a stent and is preferably expandable to facilitate its deployment. However, the cylindrical structure 33 may have any suitable structure or be formed of any suitable material which supports the valve component 35. The elements may be forced into the surrounding tissue of the heart wall by means of a dumbbell shaped inflatable balloon.

Figures 13, 14:
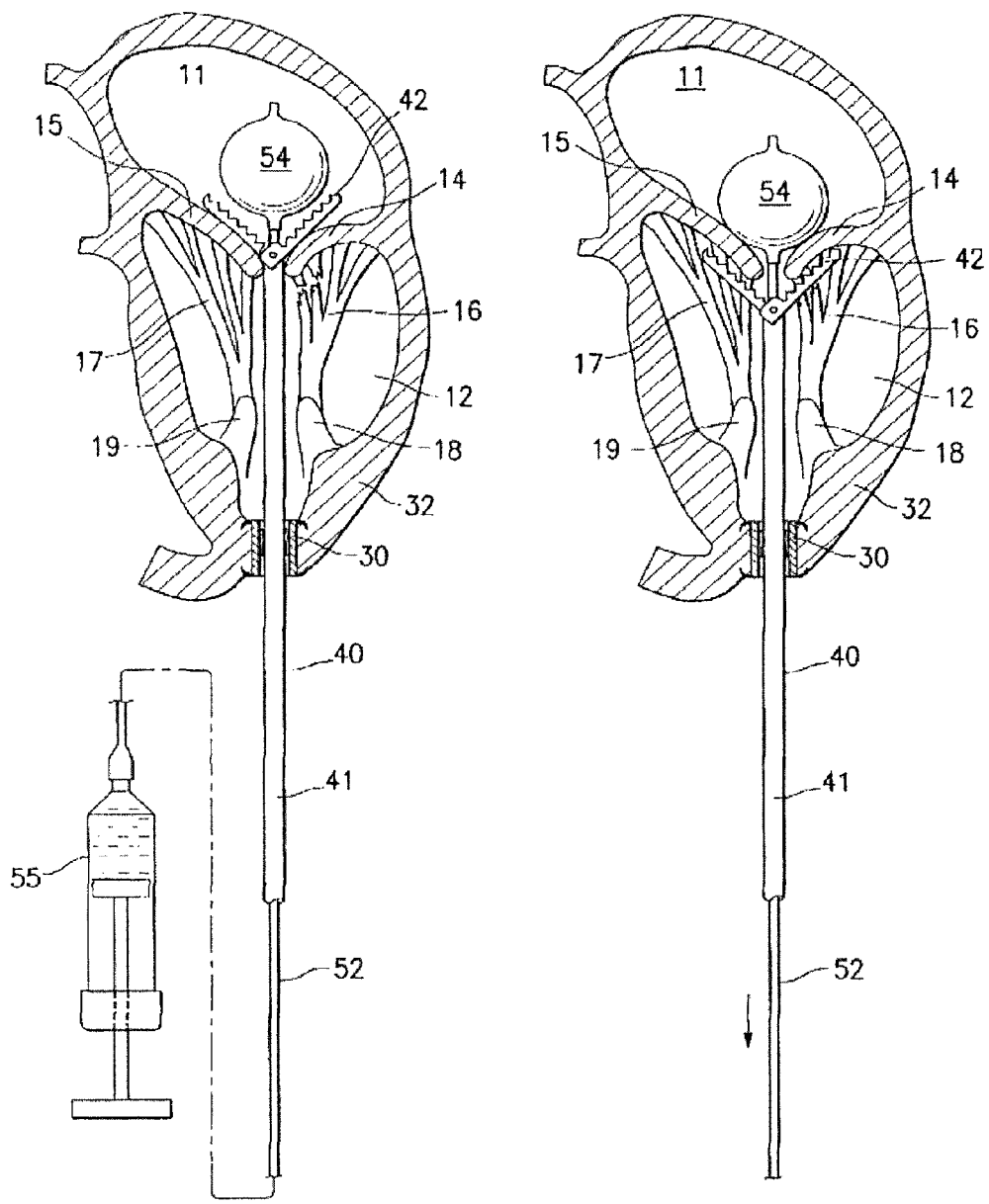
FIG. 13 is a partial elevational view, in section of the left side of a patient's heart illustrating the inflation of the balloon on the distal end of the balloon catheter within the patient's left atrium.
FIG. 14 is a partial elevational view, in section of the left side of a patient's heart illustrating the positioning of the valve leaflets in a grasping location by the balloon catheter with the expanded grasping members of the grasping device being disposed within the left ventricle in a position to grasp the valve leaflets.
Figure 21:
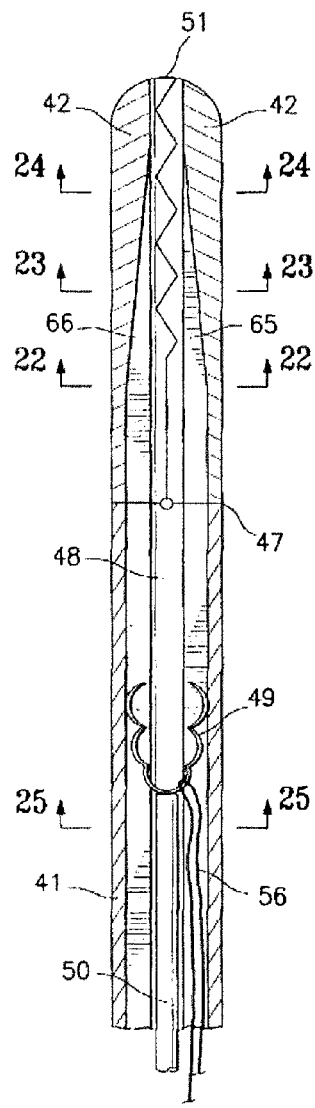
FIG. 21 is an enlarged longitudinal cross-sectional view of the distal end of the grasping device with a valve leaflet connecting member slidably disposed within the inner lumen of the grasping device.
Figure 24:
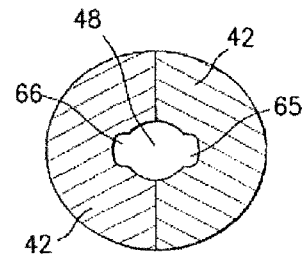
FIGS. 22-24 are transverse cross-sectional view taken along the lines 22-22, 23-23 and 24-24 of the grasping device shown in FIG. 21.
Figure 23:
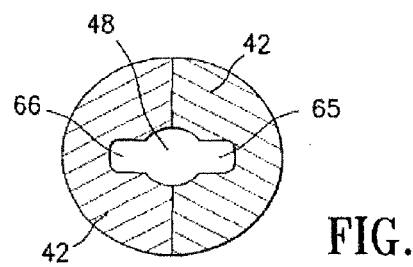
Figure 22:
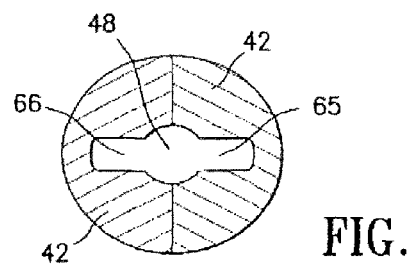
Figure 25:
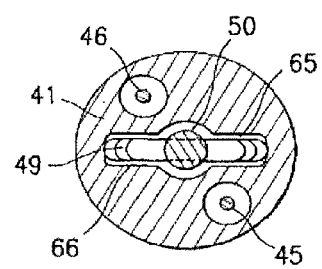
FIG. 25 is a transverse cross-sectional view taken along the lines 25-25 illustrating the pusher bar pushing the clip along the guide way lumen of the grasping device shown in FIG. 19.

FIGS. 9-18 depict a grasping device 40 which embodies features of the invention and the use of the device to secure the valve leaflets in a Bow-Tie connection. The grasping device 40 has an elongated shaft 41, a plurality of grasping members or jaws 42 on the distal portion of the shaft and finger operated handles 43 and 44 which operate the jaws 42 through pull wires 45 and 46. The grasping members or jaws 42 are pivotally mounted at the pivot point 47 on the distal end of shaft 41. While only two jaws 42 are shown, three or more jaws may be employed. The elongated shaft 41 of grasping device 40 has an inner lumen 48 extending therein to allow for the passage of instruments that aid or effect the deployment of a connecting member to the free edges of the valve leaflets to perform a Bow-Tie connection thereof as will be described in more detail hereinafter. FIG. 21 is an enlarged elevational view in section to illustrate the leaflet clip 49 and the pusher bar 50 which pushes the clip through the inner lumen 48. As shown in more detail in FIGS. 22-25, tapered grooves 65 and 66 are provided in the jaws 42 so that, as the clip 49 is pushed toward the distal ends of the jaws 42, the clip slides along the tapering grooves and is closed against free edges 21 and 22 of the leaflets 14 and 15 grasped by the jaws. The deployed leaflet clip 49 closed against the free leaflet edges 21 and 22 in a Bow-Tie connection is shown in FIGS. 17 and 18. The inner lumen 48 continues through the jaws 42 to a port 51 to allow passage of other instruments such as the distal portion of the balloon catheter 52 which positions the leaflets 14 and 15 in the grasping location as shown in FIG. 14.

Figure 10:
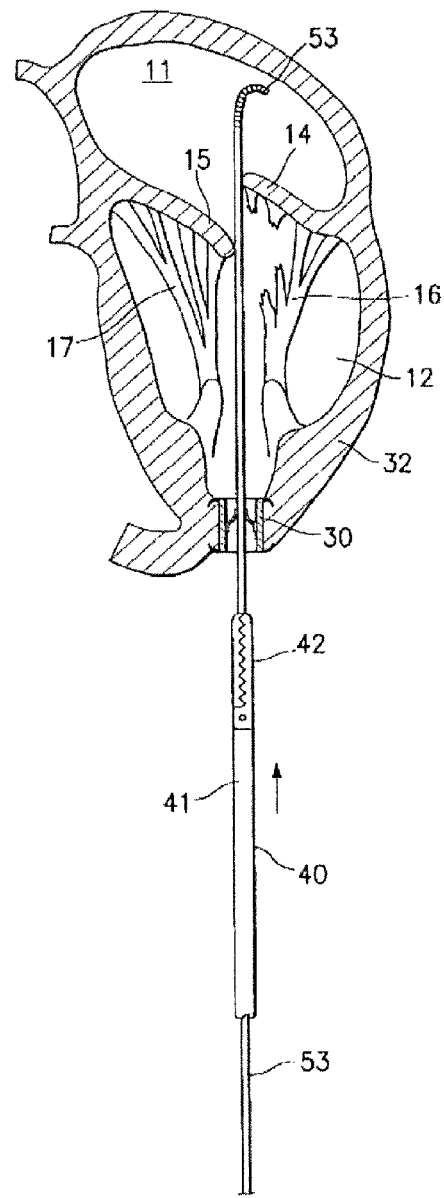
FIG. 10 is a partial elevational view, in section of the left side of the patient's heart illustrating the advancement of a grasping device over the guide wire shown in FIG. 9.
Figures 11, 12:
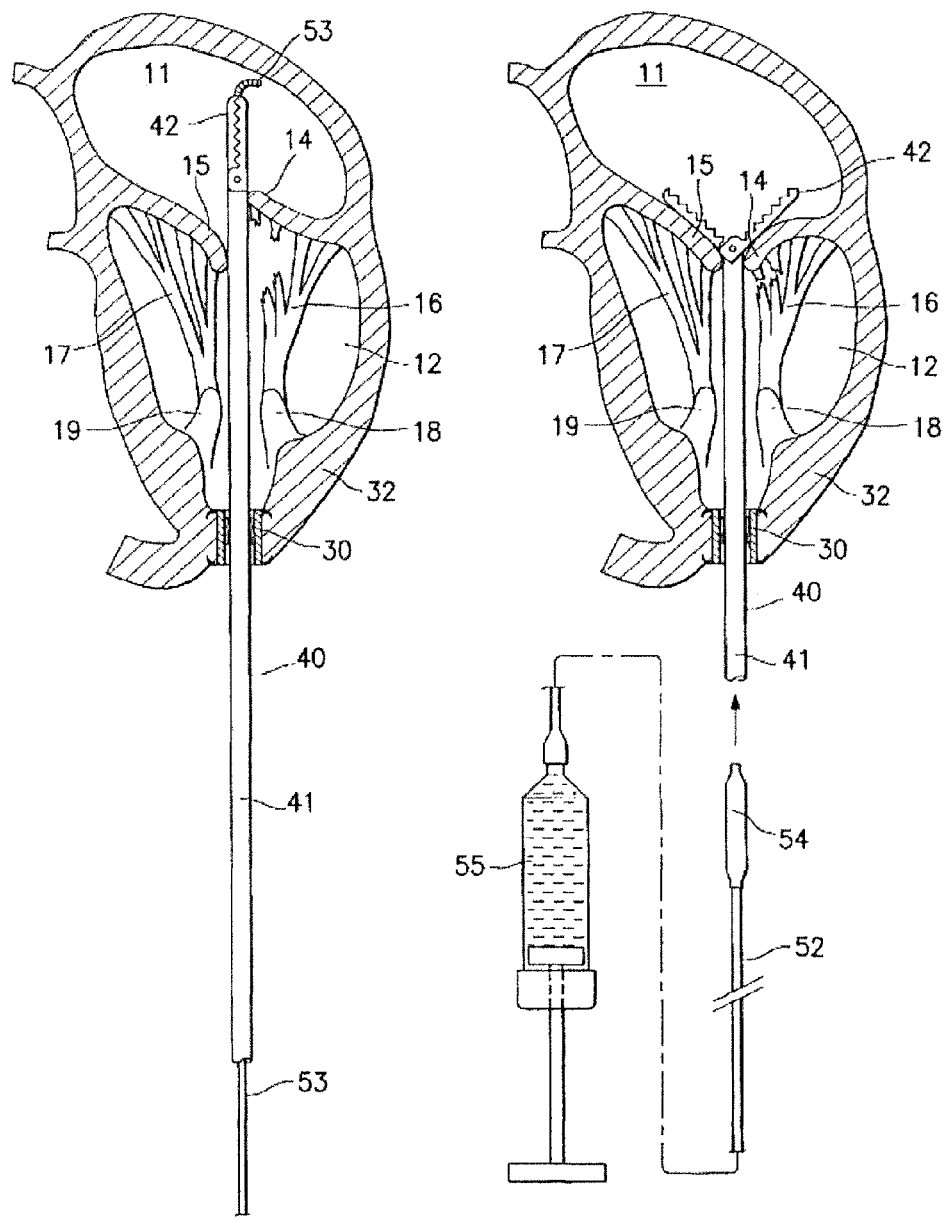
FIG. 11 is a partial elevational view, in section of the left side of the patient's heart illustrating the positioning of the grasping members on the distal end of the grasping device shown in FIG. 10 over the guide wire into the patient's left atrium.
FIG. 12 is a partial elevational view, in section of the left side of the patient's heart illustrating the advancement of a balloon catheter into an inner lumen of the grasping device for deployment within the patient's left atrium.

The use of the grasping device 40 is illustrated in FIGS. 10-18. After the one-way valve 30 is properly secured within the passageway 31 through the ventricular wall 32, a guide wire 53 is advanced through the valve 30 into the left ventricle 12 and further advanced through the mitral valve 13 into the left atrium 11 as shown in FIG. 10. A grasping device 40 is mounted on the proximal end of the guide wire 53 which extends out of the patient and is slidably advanced over the guide wire through the valve 30, and into the left atrium through the mitral valve 13. The guide wire 53 at that point is slidably disposed within the inner lumen 48 of the grasping device 40. A balloon catheter 52 may then be advanced over the guidewire 53 through the inner lumen 48 of the grasping device 40 until the inflatable balloon 54 on the distal portion of catheter 52 is disposed in the left atrium. The balloon 54 is inflated by injecting inflation fluid through an inner lumen (not shown) in the shaft of the balloon catheter 52 by means of the syringe 55 as shown in FIG. 14. If the shaft of the balloon catheter 53 is stiff enough, the guide wire 53 may be withdrawn prior to insertion of the balloon catheter 52 and the catheter advanced through the inner lumen 48 of grasping device 40 by itself.

Figure 15:
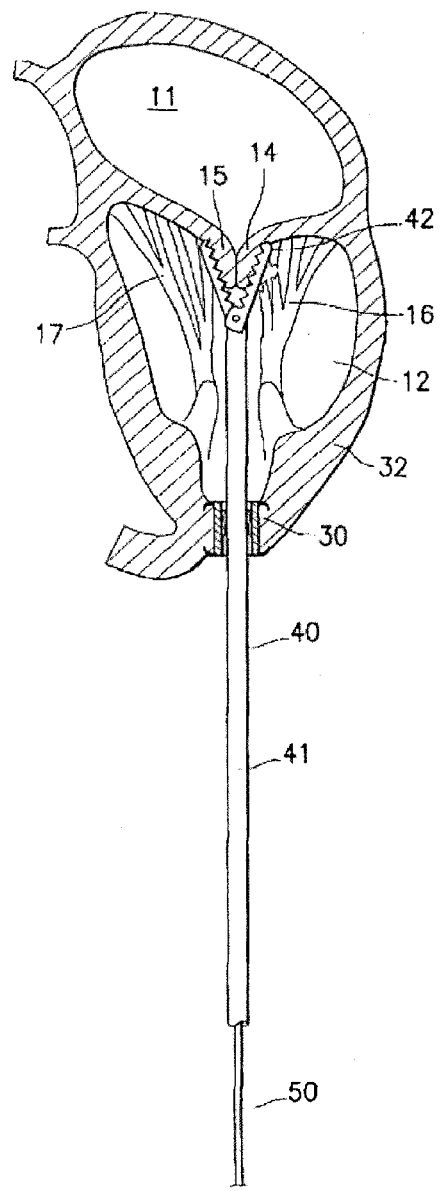
FIG. 15 is a partial elevational view, in section of the left side of a patient's heart illustrating the grasping of the valve leaflets by the grasping members of the grasping device.
Figure 16:
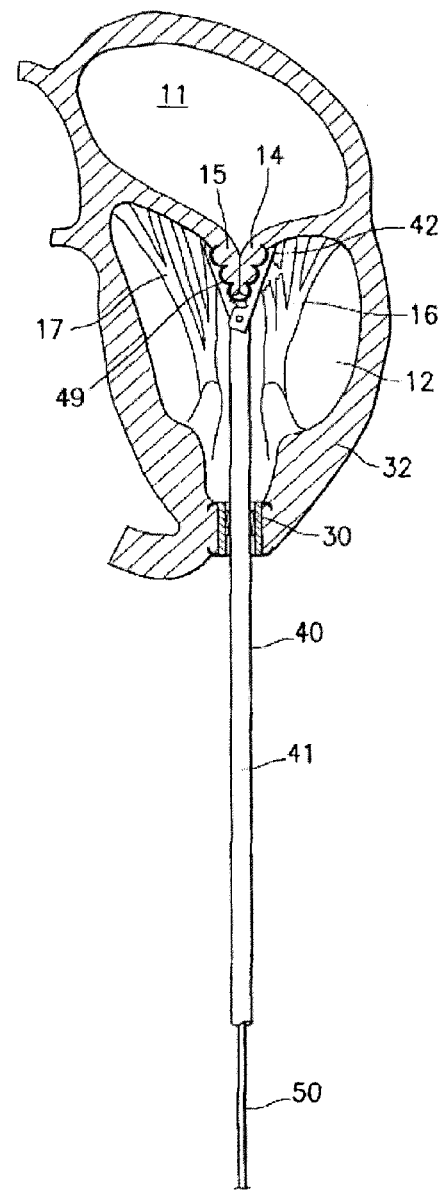
FIG. 16 is a partial elevational view, in section of the left side of a patient's heart illustrating the connecting the free edges of the valve leaflets with a clip in a Bow-Tie arrangement.

After the balloon 54 is inflated within the left atrium 11, the shaft of the balloon catheter 52 is pulled proximally to press the inflated balloon 54 against the atrial side of the mitral valve leaflets 14 and 15 to urge the leaflets into grasping location as shown in FIG. 14. The jaws 42 may then be closed on the valve leaflets 14 and 15 as shown in FIG. 15. As previously described, the leaflet clip 49 may be advanced through the inner lumen 48 by pusher bar 50 to close the clip 49 against and through the grasped free edges 21 and 22 as shown in FIGS. 17 and 18. After the clip 49 has been deployed to form the Bow-Tie connection, the grasping device 40 and any other devices that may be present are withdrawn from the patient's heart through the valve 30. The duck-billed valve component 35 closes down after removal of the various instruments and prevents loss of blood from the left ventricle. If desired, the valve 30 may be removed and the proximal opening of the ventricular passageway sutured closed.

Figure 27:
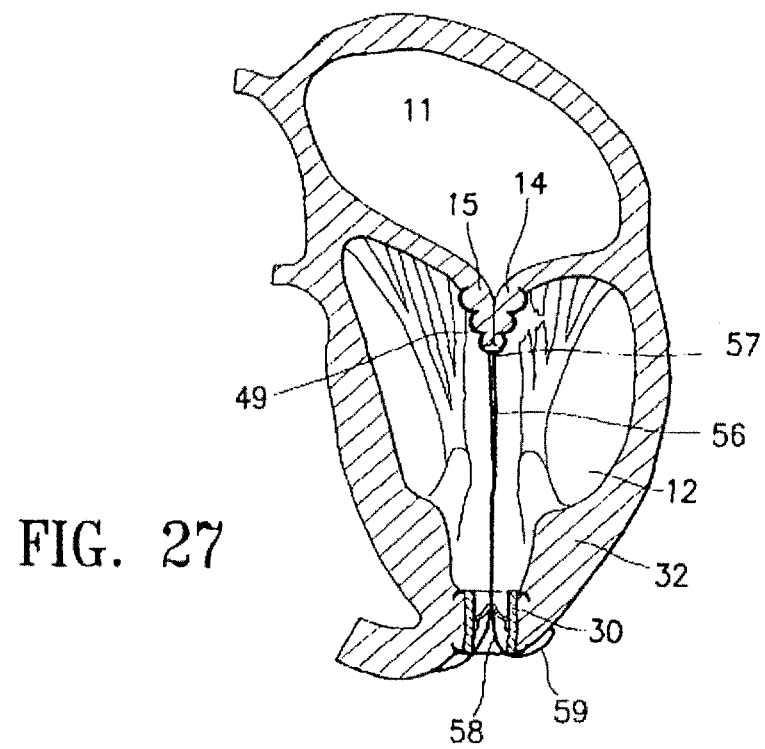
FIG. 27 is a partial elevational view, in section of the left side of a patient's heart illustrating the artificial cordae tendenae extending from the clip to the exterior of the patient's heart.

In an alternative embodiment is shown in FIG. 27 wherein an elongated strand 56 formed of relatively non-compliant material may have one end 57 secured to the closed end of leaflet clip 49. After deployment of the clip 49 to connect the free edges 21 and 22 of the leaflets 14 and 15 in a Bow-Tie connection, the proximal end 58 of the strand 56 is pulled taut to position the leaflets 14 and 15 in a natural position to ensure proper closure during systole and then the proximal end 58 of the strand 56 is secured to the free ventricular wall 32, preferably to the exterior thereof, such as shown suturing with a pledget 59. This embodiment is particularly suitable in those instances wherein cordae tendenae connected to the valve leaflet are torn. The strand 56 then acts as an artificial cordae tendenae to the leaflet. However, care must be exercised when securing the proximal end 58 of the strand 56 is secured to the heart wall 32 that the valve leaflets are in a natural position so as to prevent or reduce regurgitation through the valve 13.

The hearts of many CHF patients exhibit intraventricular conduction delay with resulting disturbance of the synchronous right and/or left ventricular contractility. As previously mentioned, a large population of the CHF patients are not suitable candidates for or fail percutaneous delivery of pacing leads to provide relief from CHF. In these instances, it has been found that a pacing lead secured to the exterior wall defining in part the heart chamber exhibiting the conductance delay can better control the contraction of the heart to improve the chamber's ejection.

Figure 28:
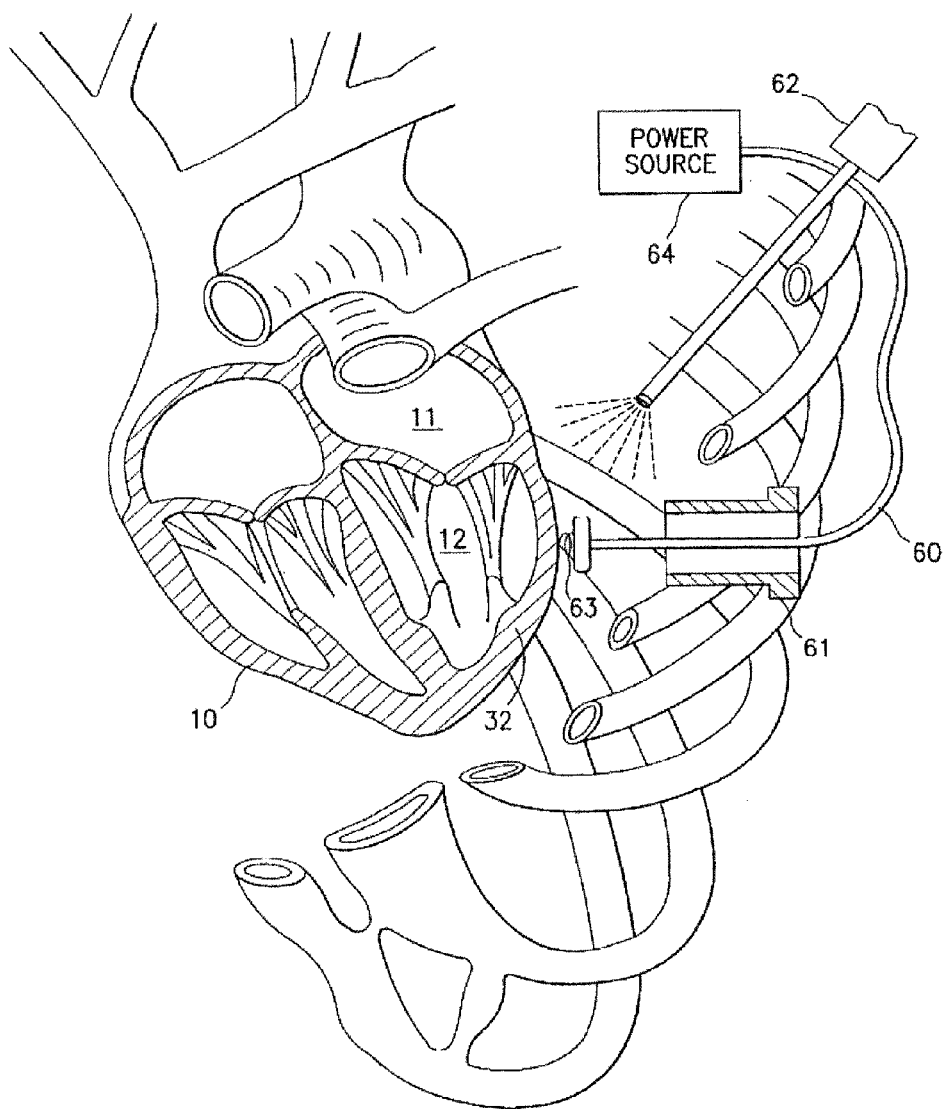
FIG. 28 is a perspective view of a patient's chest, partially illustrating the location of the patient's heart within the chest cavity, with part of the heart wall removed to expose the left ventricular chamber and illustrating placing the penetrating electrode of a pacing lead within the heart wall defining in part the left ventricle.

As shown in FIG. 28, the pacing lead 60 can be deployed within the patient's chest cavity by minimally invasive techniques through a trocar 61 located in the intercostal space between the patient's ribs. The placement of the pacing lead 60 can be observed by an endoscopic video 62 extending through an intercostal space. Instruments to facilitate the implantation of the helically shaped electrode 63 of the pacing lead 60 can be passed through the trocar 61 and the electrode secured within the heart wall 32 by minimally invasive techniques. The pacing lead 60 has its proximal end configured to be electrically connected to a pacing power source 64 which is preferably disposed at a subcutaneous location. The pulsed output of the power source 64 may be controlled in a conventional manner to provide the desired contractions to the heart wall to which the pacing lead is secured.

Figure 29:
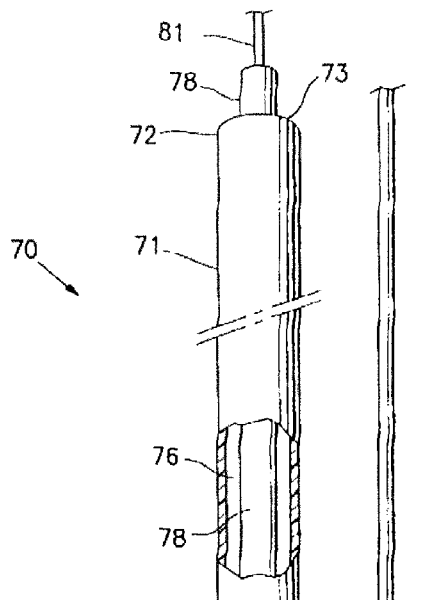
FIGS. 29-31 illustrate a suitable minimally invasive device for implating a pacing lead in a patient's heart wall.
Figure 29:
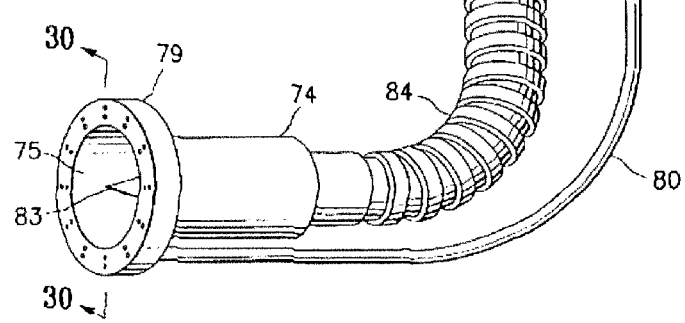
Figure 30:
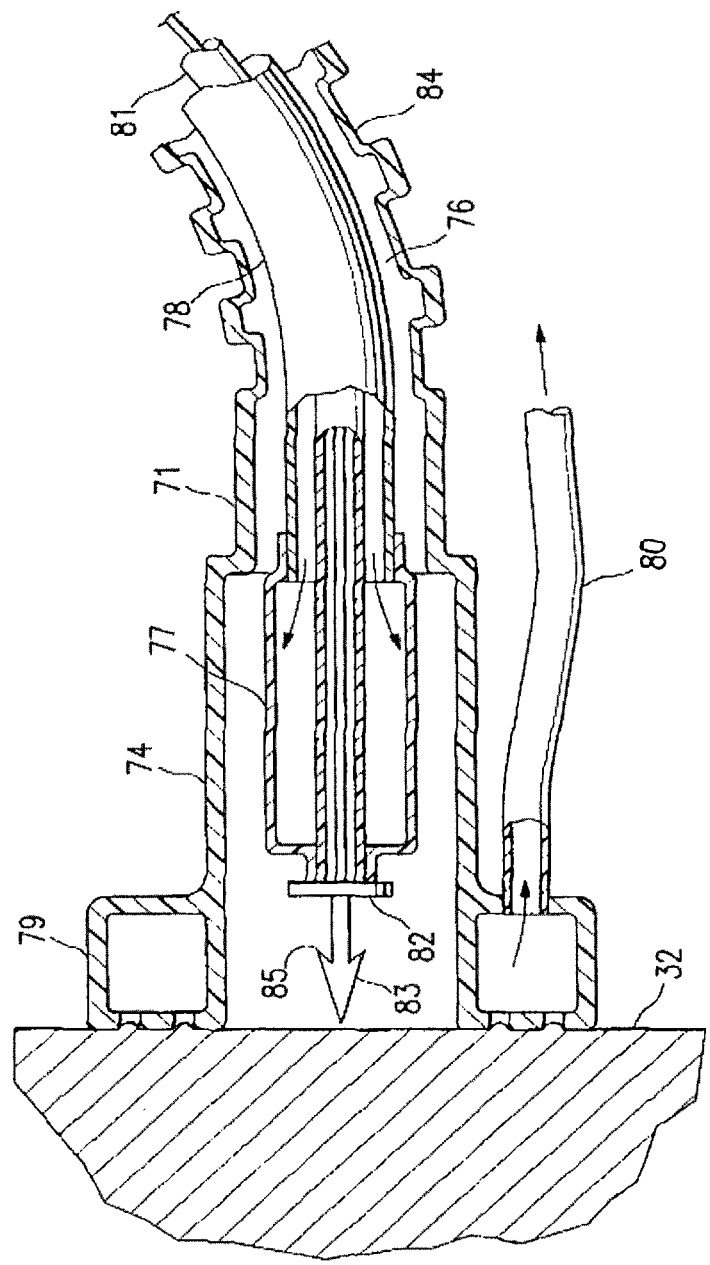
Figure 31:
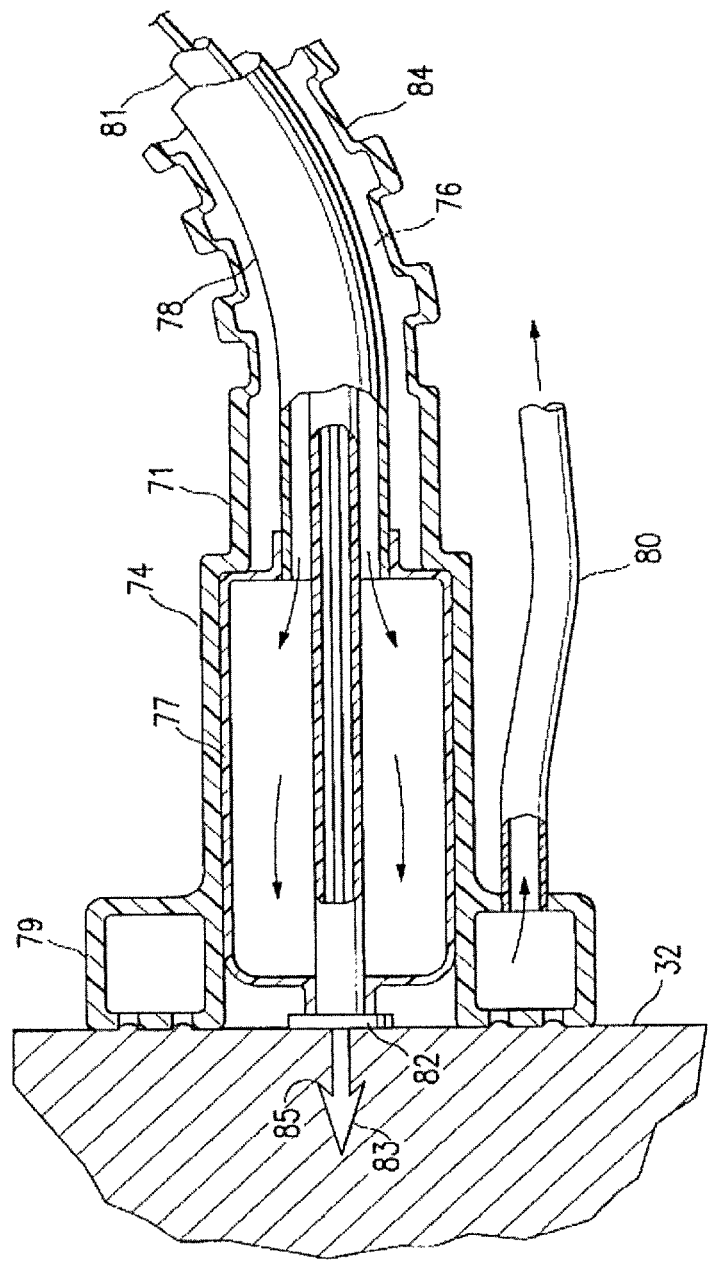

FIGS. 29 to 31 illustrate a minimally invasive embodiment having features of the invention to secure an electrode of a pacing lead within the free wall defining the left ventricle of the patient's heart to control the contraction of the left ventricle and improve the output thereof. This device 70 includes a tubular delivery member 71 having a proximal end 72 with a port 73, an enlarged distal end 74 with a port 75 and inner lumen 76 extending within the tubular member from the proximal port 73 to the distal port 75. The distal end of the tubular member 71 is enlarged to receive a longitudinally expansive member such as inflatable balloon 77. The balloon 77 is provided with an elongated shaft 78 having an inner inflation lumen (not shown) which allows inflation fluid to be introduced into the interior of the balloon to inflate the balloon. The distal end of tubular member 71 is provided with a vacuum pod 79 to secure the distal end to the exposed surface of the free ventricular wall 32. The interior of the pod 79 is connected to the vacuum tube 80 which is in turn configured to be connected to a vacuum source (not shown). The pacing lead 81 has a collar 82 secured about a distal portion thereof which is configured to be engage by the balloon 77 when the latter is inflated to drive the penetrating electrode 83 on the pacing lead against the exposed ventricular wall 32 so that the penetrating electrode 83 penetrates into and is secured within the ventricular wall. The tubular member 71 may have a flexible section 84 to facilitate articulation of the distal extremity of the tubular member 71 to aid in the placement of the vacuum pod 79 to the exterior of the heart wall 32. The vacuum pod 79 is configured to pass through a trocar provided in an intercostal space between the patient's ribs.

The pacing lead 81 shown in FIGS. 29-31 is installed by first making a small opening in the patient's chest and implacing a first trocar (not shown) having an inner lumen. Commercially available trocars include trocars from U.S Surgical and others. A second similar trocar (not shown) is installed in a similar manner for a thoroscope such as shown in FIG. 28, which allows the operating surgeon to view the region in which the pacing lead is to be installed and to place a variety of instruments within the patient's chest cavity. Other trocars may also be installed for other purposes.

The lower left lobe of the patient's lung is moved out of the way to expose the patient's heart. The pericardium on the free wall 32 defining in part the patient's left ventricle is removed from the desired epicardial site in which the pacer lead is to be secured. The pacer lead delivery tube 71 is introduced into the patient's chest cavity through the first trocar and advanced within the chest cavity toward the exposed epicardial surface. The open end of the vacuum pod 79 on the expanded distal end of the delivery tube is pressed against the exposed epicardial surface and a vacuum is developed within the inner chamber of the pod to hold the distal end of the tubular member 71 against the epicardial surface. Inflation fluid is introduced into the interior of the balloon 77 through the inflation lumen in tube 78. The expanded distal end 74 of the delivery tube 71 limits the radial expansion of the balloon, so the balloon expands longitudinally in the distal direction as shown in FIG. 31. The longitudinal expansion causes the distal end of the balloon to expand against the flange secured to the distal portion of the pacer lead. Balloon pressure on the collar 82 drives the pacing lead toward the epicardial location on the exterior of the patient's heart and the penetration electrode 83 on the distal end of the pacing lead into the ventricular wall. The barbs 85 on the penetration electrode secure the electrode within the heart wall and prevent the electrode from being pulled out of the wall. Electrical pulses from a suitable electrical power source are applied to the proximal end of the pacer lead. The electrical pulses are transmitted through the pacing lead conductor to the electrode secured within the heart wall. The pulses are emitted from the secured electrode into the tissue of the heart wall to pace the patient's left ventricle. The pacing is controlled in order to increase the volume of blood pumped out of the heart chamber.

An alternative device 90 is shown in FIGS. 32 and 33 which has an elongated tubular shaft 91 with a proximal end 92, a distal end 93, a semispherical shaped housing 94 on the distal end with an annular vacuum chamber 95 around the lower edge of the semi-spherical housing. An inner lumen 96 extends through the tubular shaft 91 which is in fluid communication with the vacuum chamber 95 in the housing. The proximal end 92 of the tubular member 91 is configured to be connected in fluid communication with a vacuum source (not shown). A second tubular member 97 extends through the tubular member 91 and is connected in fluid communication with the interior of balloon 98 located within the semi-spherical housing in order to direct inflation fluid thereto. A pacing lead 99 extends along, but exterior to, the tubular member 91 and has a distal end with a balloon support platform 100 and a tissue penetrating electrode 101 extending away from the platform. The distal portion of the tubular shaft is provided with some degree of flexibility in order to ensure that the spherical housing is in a proper orientation to be pressed against the exposed epicardial surface for sealing the vacuum chamber against the surface. With the vacuum chamber secured against the epicardial surface 32, the balloon 98 is inflated to drive the supporting platform 100 and the connected penetrating electrode 101 toward the epicardial surface. The electrode 101 is driven into the wall of the patient's left ventricle and the barbs 104 thereon secure the electrode within the wall tissue to prevent its removal. Electrical pulses from a suitable power source may then be applied to the tissue within the heart wall to pace the contraction thereof as discussed above to increase the output of blood from the heart chamber. The balloon 98 is releasably secured to the support platform 100 so that when the electrode is driven into the heart wall, the balloon can be deflated and the vacuum within the vacuum chamber of the semi-spherical housing may be released and the assembly withdrawn from the patient through the trocar through which it was delivered. The proximal end of the pacing lead may then be directed to the power source and connected thereto.

Figure 34:
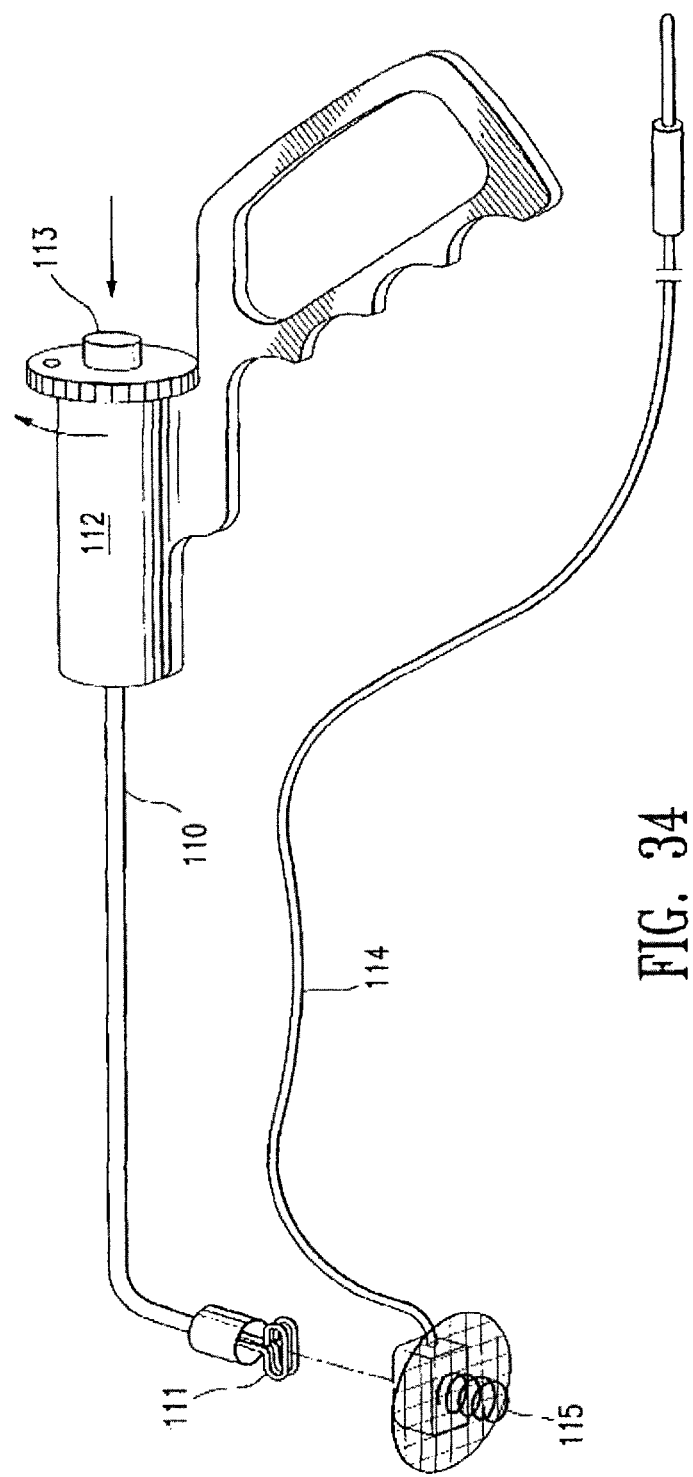
FIG. 34 illustrates another minimally invasive device for implating a pacing lead in a patient's heart wall.

Another alternative embodiment is shown in FIG. 34, which has an elongated tube 110 with a grasping mechanism therein and a pair of grasping tongs 111 on the distal end of the mechanism configured to be secured to a pacing lead. The embodiment has a housing 112 on the proximal end with a rotating lead holder which when rotated rotates the pair of tongs 111 on the distal end of the mechanism. A button 113 is provided to disengage the tongs from the pacing lead 114. The rotation of the tongs 111 causes the rotation of the pacing lead and the helical electrode 115 to screw into the heart wall. This device will soon be offered by Medtronic as an epicardial lead implant tool (Model No. 10626) which is designed to be used with a Model 5071 pacing lead.

Usually an additional (conventional) pacing lead is installed in the patient's right ventricle for complete resynchronization of the heart chambers. The additional lead is preferably connected to the same power source as the first described pacing lead which may be located in the infraclavicular pocket in a conventional manner.

EXAMPLE

Twenty patients were selected (12 men, 8 women) for thorocoscopically direct left ventricular lead placement. The patients had New York Heart Association Class III or IV congestive heart failure with a mean ejection fraction of 20%.+−.8%. All of the patients had previously undergone transvenous right-ventricular lead placement and subcutaneous implantation of a dual or triple chamber pacement but had failed transvenous left-ventricular lead placement due to suboptimal coronary vein anatomy. Surgical entry into the left chest was carried out through a 2 cm incision in the mid acillary line at the sixth intercostal space, following collapse of the left lung. A 15 mm thoracoport (U.S. Surgical) was inserted with the tip of the trocar pointing to the left should to minimize contact with the heart. A 5 mm rigid port was inserted inferolateral to the left nipple of the patient in the sixth intercostal space to allow insertion of a grasper such as the U.S. Surgical Endograsper. Another 5 mm rigid port is inserted in the fourth intercostal space at the anterior axillary line for a scope and camera. A portion of the pericardium was removed to provide an exposed epicardial region for implantation of the helical electrode of the pacing lead. Screw in epicardiac leads (Medtronic 5071 and Guidant 4047) were inserted under video control through the 15 mm trocar or rigid port. The leads were inserted into the epicardium by applying gentle pressure and three clock-wise full rotations of the pacing lead holder. If pacing voltage thresholds were unacceptably high the pacing lead would be twisted one-quarter turn and then retested. Acceptable pacing lead placement is defined as 100% pacing at 2.5 volts or less. The video assisted left-ventricular lead placement was successful in nineteen of the twenty patients. The one failure required an open thoracotomy.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for accessing a left ventricle of a heart, said method comprising:
   placing a valve structure having a tissue-penetrating securing element through a passageway in an apical wall of the heart;
   penetrating the securing element into tissue surrounding the valve structure in the apical wall to secure the valve structure in the passageway; and
   introducing a tool through the valve structure into the left ventricle;
   wherein the valve structure has an exit flush with an inner surface of the left ventricle and an entrance flush with an outer surface of the heart.

2. The method as in claim 1, wherein the securing element is attached to an outer surface of the valve structure.

3. The method as in claim 2, wherein the securing element is disposed circumferentially about a cylindrical wall of the valve structure.

4. The method as in claim 3, wherein the securing element comprises a plurality of hooks or barbs.

5. The method as in claim 1, wherein the valve structure comprises a one-way valve.

6. The method as in claim 5, wherein the one-way valve comprises a duck bill valve.

7. The method as in claim 1, wherein introducing the tool comprises engaging a heart valve.

8. The method as in claim 7, wherein engaging the heart valve comprises repairing an incompetent heart valve.

9. The method as in claim 8, wherein the incompetent heart valve comprises a mitral valve.

10. The method as in claim 1, wherein introducing the tool comprises a procedure selected from the group consisting of transmyocardial revascularization, aortic stenting for aortic dissections and aneurysm therapy, removal of clots and vegetations from prosthetic valves, excision of heart tumors, implantation of stem cell and vascular growth factors, and closure of ventricular septal defects.

* * * * *